US011241462B2

(12) United States Patent
Madhavamenon et al.

(10) Patent No.: US 11,241,462 B2
(45) Date of Patent: Feb. 8, 2022

(54) SYNERGISTIC CURCUMINOIDS AND PROBIOTIC COMPOSITIONS

(71) Applicant: Akay Flavours & Aromatics Pvt., Ltd., Cochin (IN)

(72) Inventors: Krishnakumar Illathu Madhavamenon, Cochin (IN); Balu Paulose Maliakel, Cochin (IN)

(73) Assignee: AKAY FLAVOURS & AROMATICS PVT, LTD, Kerala (IN)

( * ) Notice: Subject to any disclaimer, the term of this patent is extended or adjusted under 35 U.S.C. 154(b) by 279 days.

(21) Appl. No.: 16/232,885

(22) Filed: Dec. 26, 2018

(65) Prior Publication Data

US 2019/0192588 A1 Jun. 27, 2019

(30) Foreign Application Priority Data

Dec. 27, 2017 (IN) .............................. 201741034225

(51) Int. Cl.
| | | |
|---|---|---|
| *A61K 35/00* | (2006.01) | |
| *A61K 9/00* | (2006.01) | |
| *A61K 9/16* | (2006.01) | |
| *A23L 33/135* | (2016.01) | |
| *A61K 35/747* | (2015.01) | |
| *A61K 31/12* | (2006.01) | |
| *A61K 35/744* | (2015.01) | |
| *A61K 35/741* | (2015.01) | |
| *A61K 31/00* | (2006.01) | |
| *A61K 36/9066* | (2006.01) | |
| *A61K 35/745* | (2015.01) | |
| *A61K 36/48* | (2006.01) | |
| *A23L 33/00* | (2016.01) | |
| *A61K 35/742* | (2015.01) | |
| *A61K 9/14* | (2006.01) | |
| *A61K 9/107* | (2006.01) | |
| *A61K 35/12* | (2015.01) | |
| *A61K 47/46* | (2006.01) | |

(52) U.S. Cl.
CPC ............ *A61K 35/747* (2013.01); *A23L 33/00* (2016.08); *A61K 9/0053* (2013.01); *A61K 9/1652* (2013.01); *A61K 9/1664* (2013.01); *A61K 31/00* (2013.01); *A61K 31/12* (2013.01); *A61K 35/741* (2013.01); *A61K 35/742* (2013.01); *A61K 35/744* (2013.01); *A61K 35/745* (2013.01); *A61K 36/48* (2013.01); *A61K 36/9066* (2013.01); *A61K 9/1075* (2013.01); *A61K 9/148* (2013.01); *A61K 47/46* (2013.01); *A61K 2035/115* (2013.01); *A61K 2035/128* (2013.01)

(58) Field of Classification Search
CPC .... A61K 9/1652; A61K 9/0053; A61K 31/12; A61K 47/46; A61K 36/48; A61K 9/1075; A61K 9/148; A61K 2035/128; A61K 35/741; A61K 36/9066; A61K 2035/115; A61K 35/747; A61K 35/742; A61K 35/744; A61K 31/00; A61K 9/1664; A61K 35/745; A61K 2300/00; A23L 33/00; A23L 33/105; A23L 33/20; A23L 33/135
See application file for complete search history.

(56) References Cited

U.S. PATENT DOCUMENTS

| | | |
|---|---|---|
| 8,785,380 B2 | 6/2014 | Krishnakumar et al. |
| 2012/0263826 A1 | 10/2012 | Fang et al. |
| 2013/0029905 A1* | 1/2013 | Madhavamenon et al. ... 514/5.5 |
| 2017/0296598 A1 | 10/2017 | Krishnakumar et al. |

OTHER PUBLICATIONS

Maha B., Antidiabetic potential of turmeric with/without fermented milk enriched with probiotics in diabetic rats, American Journal of Biomedical and Life Sciences, 2013; vol. 1, No.1, pp. 1-7. (Year: 2013).*
Vidyalaxme B. et al., "Synergistic effects of probiotic Leuconostoc mesenteroides and Bacillus subtilis in malted ragi (Eleucine corocana) food for antagonistic activity against V. cholerae and other beneficial properties", J Food Sci Technol., Nov. 2014, vol. 51, No. 11, pp. 3072-3082. (Year: 2014).*
Sudheeran, et al., "Safety, tolerance, and enhanced efficacy of a bioavailable formulation of curcumin with fenugreek dietary fiber on occupational stress" *Journal of Clinical Psychopharmacology*, 36(3): 236-243 (2016).
Krishnareddy, et al., "A novel curcumin-galactomannoside complex delivery system improves hepatic function markers in chronic alcoholics: a double-blinded, randomized, placebo-controlled study," *BioMed Research International*, 1-10 (2018).
Krishnakumar et al., "Improved blood-brain-barrier permeability and tissue distribution following the oral administration of a food-grade formulation of curcumin with fenugreek fibre,"*Journal of functional foods*, 14:215-225 (2015).

\* cited by examiner

*Primary Examiner* — Satyendra K Singh
(74) *Attorney, Agent, or Firm* — Crowell & Moring LLP

(57) ABSTRACT

The current invention relates to the field of a novel probiotic-curcuminoids formulation, which exhibits increased curcuminoids bioavailability, and viable probiotic microbial population in the presence of curcuminoids. The probiotic-curcuminoids formulation is made by encapsulation in ragi and galactomannan-rich fenugreek dietary fiber matrix. Compositions and methods for making this formulation are also disclosed herein.

11 Claims, 1 Drawing Sheet

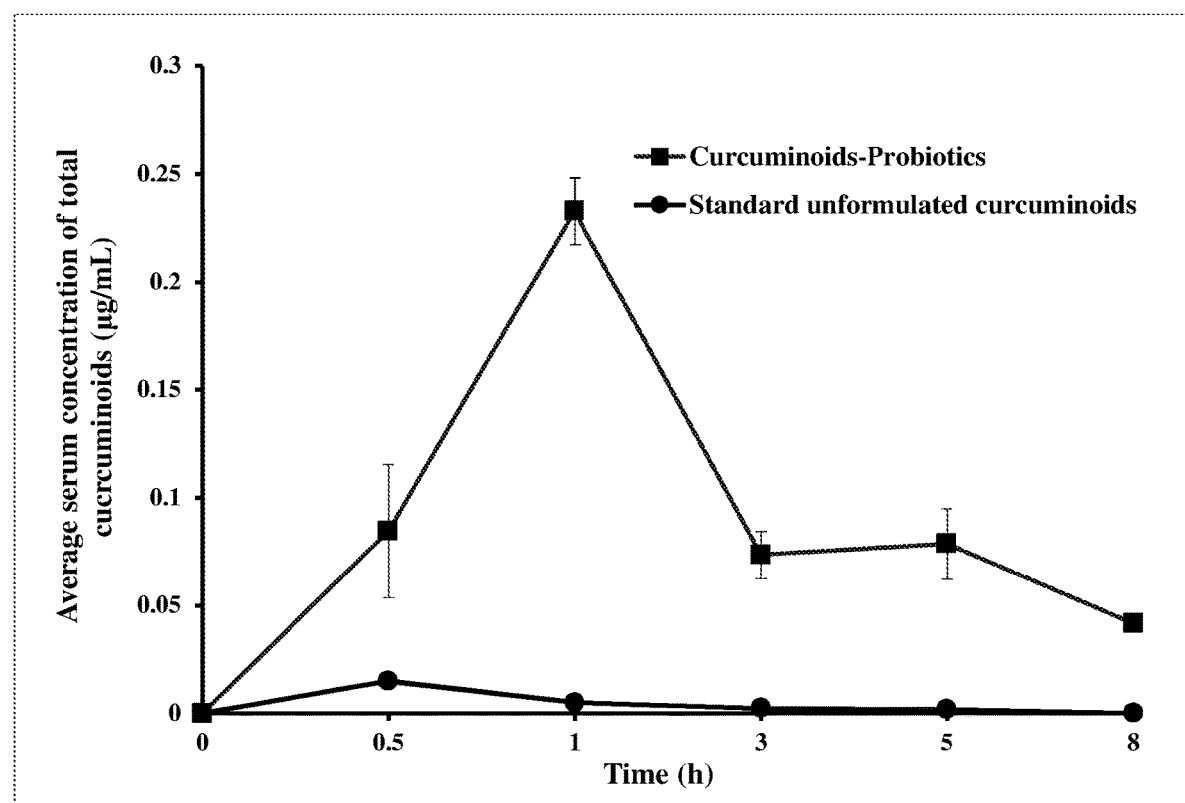

SYNERGISTIC CURCUMINOIDS AND PROBIOTIC COMPOSITIONS

CROSS-REFERENCE TO RELATED APPLICATION

The present application claims priority to Indian Provisional Patent Application No. 201741034225 filed on Dec. 27, 2017, the full disclosure of which is hereby incorporated by reference herein.

FIELD OF INVENTION

The present invention relates to the field of probiotic formulations that contains probiotic microorganisms along with curcuminoids, the yellow pigment and the bioactive principle of turmeric. Galactomannan-rich fenugreek fiber and ragi are used to encapsulate curcuminoids along with probiotic bacteria, which ensures viable probiotics in the presence of curcuminoids and increased their bioavailability.

BACKGROUND OF THE INVENTION

Curcumin or diferuloylmethane, the main bioactive constituent and yellow pigment in turmeric or *Curcuma longa* L (Zingiberaceae family), is generally obtained from dried turmeric rhizomes by solvent extraction as a as a mixture of three molecules namely, curcumin (76-80% w/w), demethoxycurcumin (12-15% w/w) and bisdemethoxycurcumin (2 to 5% w/w) and is very often referred to as "curcuminoids". The total curcuminoids content of not less than 95% is the standard form of curcuminoids, sometimes also called curcumin, generally in use as dietary supplements and nutraceuticals.

The turmeric root is a traditional and popular spice in India and other Asian countries. Curcumin is known to have anti-microbial, anti-diabetic, anti-inflammatory, anticancer, antioxidant, anti-arthritic, anti-atherosclerotic, anti-depressant, anti-aging, wound healing and memory-enhancing activities. Ever since the identification of curcumin as the main constituent of turmeric, multiple pharmacological activities of curcumin that include antimicrobial, anti-diabetic, anti-inflammatory, anticancer, and antioxidant properties have been reported. In combination with other drugs, curcumin has also been reported to enhance the effects of antibacterial, antifungal, anti-inflammatory, anticancer, and antioxidant activities. These properties have been most extensively and exhaustively studied as evidenced by thousands of publications. Curcumin is being widely used as a health supplement owing to its antioxidant and anti-inflammatory properties. Besides, curcumin exhibits low to no toxicity at the active doses as substantiated in earlier studies.

However, benefits of curcumin are hugely hindered by its color, poor solubility in water and poor bioavailability. The low bioavailability of curcumin might be primarily due to its poor absorption, fast metabolism and rapid systemic elimination contributed by the hydrophobicity and highly mobile chemical structure.

Various approaches have been employed including the use of adjuvants, liposomes, nanoparticles and phospholipid complexes to overcome this limitation. The galactomannoside dispersion of curcuminoids is proven to enhance the bioavailability of curcuminoids; hence enhances the therapeutic efficacy. (U.S. Pat. No. 8,785,380B2; Naveen et al, BioMed Research International, 2018; https://doi.org/10.1155/2018/9159281; Sudheeran et al, J Clinical Psychopharmacology, 2016, 36 (3), 236-243).

US20170296598A1 discloses the probiotic powder compositions encapsulated in the cereal matrix.

Probiotics, which are live nonpathogenic microorganisms, when administered in adequate amounts, confer microbial balance, particularly in the gastrointestinal tract. The gut microbiota homeostasis is very important in the gastric health and hence overall health. Disruption of this balance has been reported to have adverse effects on the normal functioning of body.

Studies have shown that consumption of probiotics results in improving immunity by lowering the frequency and duration of diarrhea, stimulating humoral and cellular immunity, preventing cancer and helping eliminate unfavorable metabolites, including ammonium and procarcinogenic enzymes in the colon. Probiotics that colonize the intestinal tract, have also been reported to have a beneficiary effect against metabolic diseases such as obesity and diabetes. Lactic acid bacteria strains represent most of the probiotics both in the food and pharmaceuticals available presently. They are known to help combat ulcerative colitis (UC), metabolic diseases and are beneficial in improving the growth, immune system and antioxidant status. Additionally, recent studies have helped understand the antioxidant capacity of probiotics. *Lactobacillus* strains were revealed to resist ROS, including superoxide anions, peroxide radicals and hydroxyl radicals. They were also found to confer protection to liver and lower lipid accumulation in high fat fed animal models. Under elevated physical stress, *Lactobacillus* has been shown to increase antioxidant levels in humans, thereby neutralizing the effects of reactive oxygen species.

Finger Millet (*Eleusine africana*), commonly known as 'ragi' in India, is a rich source of protein, fiber, carbohydrates and minerals like calcium and iron. The cereal has low fat content and contains mainly unsaturated fat. In vitro and in vivo (animal) studies have shown lowering of blood glucose and cholesterol, anti-ulcerative, wound healing properties, etc., on consumption of finger millet. Ragi contains an amino acid tryptophan, which lowers appetite and helps in keeping weight in control. Ragi gets digested at a slower rate thus keeps one away from intake of excessive calories.

The soluble fiber extracted from fenugreek (*Trigonella foenum* gracum) is rich in galactomannans. The galactomannans of fenugreek fiber is proved to provide beneficial effects in blood glucose management, lipid profile management and gastro protective activity. It also acts as a prebiotic fiber.

Since both curcuminoids and probiotics are beneficial health supplements and offers synergistic effect, the present invention aims to develop a formulation capable of efficiently delivering both curcuminoids and probiotics in a single health supplement. Though our studies and some earlier publications have showed that curcuminoids could not be stabilized in the presence of *Lactobacillus acidophilus*, the present invention provides a unique combination of fenugreek dietary fiber rich in galactomannans and ragi extract powder for the stability, storage and simultaneous oral delivery of curcuminoids with higher oral bioavailability along with probiotics in a physiologically relevant dosage form.

The present invention overcomes the challenge of combining curcuminoids which possess the anti-bacterial activity and probiotics in a single formulation.

SUMMARY OF THE INVENTION

The primary objective of the present invention is to provide a natural food grade oral composition to co-administer curcuminoids and probiotics.

Another objective of the present invention is to develop natural materials and their compositions that can be used as a vehicle for the controlled oral delivery of curcuminoids along with probiotic bacteria.

Another objective is to develop prebiotics as a carrier for the delivery of probiotics.

Another embodiment of the present invention is to address the problem of poor oral bioavailability and poor water dispersibility of curcuminoids without using synthetic additives and emulsifiers while co-delivering the probiotics.

Another objective of the present invention is to provide compositions using fenugreek dietary fiber and ragi extract as medium for growth and matrix for stable encapsulation of curcuminoids and probiotics for their simultaneous oral delivery.

One embodiment of the current invention is a formulation comprising probiotic microorganisms and curcuminoids in powder or granular form, wherein the formulation can be administered orally. In one embodiment, galactomannan-rich fenugreek fiber and ragi matrix are used to encapsulate the curcuminoids and probiotics. In one embodiment, the encapsulating matrix also acts as a growth medium for the encapsulated probiotic microorganisms.

In one embodiment, the formulation comprises a mixture of probiotic powder and curcuminoids powder, wherein the probiotic powder comprises probiotic microorganisms encapsulated in a ragi and galactomannan-rich fenugreek fiber matrix, and wherein the curcuminoids are encapsulated in a galactomannan-rich fenugreek fiber matrix.

In one embodiment, it exhibits increased bioavailability, increased absorption and longer half-life of the encapsulated curcuminoids after oral administration, compared to that of the unformulated curcuminoids derived from turmeric rhizomes.

In one embodiment, the probiotic bacteria comprising the formulation are viable.

In one embodiment, the probiotic microorganisms in the formulation disclosed in the current invention are selected from the group consisting of *Lactobacillus acidophilus, Lactobacillus acidophilus, Lactobacillus brevis, Lactobacillus rhamnosus* GG, *Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophiles, Bacillus coagulans, Saccharomyces cerevisiae,* and *Saccharomyces boulardii*.

In one embodiment, the formulation disclosed in the current invention is administered orally at a dose of 250 mg-1000 mg/dose, and wherein at least one dose of the formulation is administered daily.

In one embodiment, one dose of the formulation disclosed in the current invention, is 250-1000 mg, and comprises at least $10^6$-$10^{12}$ cfu/g of probiotic microorganisms.

In one embodiment, the concentration of curcuminoids in the formulation disclosed in the current invention is in the range of 10 to 35% w/w.

In one embodiment, the concentration of curcuminoids in the formulation disclosed in the current invention is not less than 20% w/w.

One embodiment of the current invention is a method of preparing a formulation comprising probiotic microorganisms and curcuminoids in powder or granular form, wherein the formulation can be administered orally, the method comprising the steps of: (a) suspending powdered galactomannan-rich fenugreek fiber with particle size less than 100 microns in 10-20 times (w/v) water to obtain a homogenized galactomannan-rich fenugreek fiber gel phase; (b) preparing a free flowing 1 to 2% (w/v) galactomannan-rich fenugreek fiber solution; (c) adding curcuminoids powder to the galactomannan-rich fenugreek fiber solution from step (b) followed by homogenization to produce micellar curcuminoids solution comprising micelles smaller than 10 microns; (d) adding micellar curcuminoids solution from step (c) to the galactomannan-rich fenugreek fiber gel phase from step (a) followed by homogenization to obtain curcuminoids-fenugreek solution; (e) incubating the curcuminoids-fenugreek solution from step (d) for 2 to 4 h at 10-15° C. to obtain galactomannans-curcuminoids complexed gel; (f) converting the galactomannans-curcuminoids complexed gel from step (e) to galactomannans-curcuminoids powder; (g) making ragi extract solution from ragi seeds; (h) mixing 20% w/w ragi extract solution from step (g) with 2% w/w galactomannan-rich fenugreek fiber gel phase in step b) to make a free flowing ragi extract-galactomannan solution; (i) growing the probiotic microorganisms in the free-flowing ragi-extract-galactomannan solution from step (h) to obtain probiotic-ragi-galactomannan solution; (j) drying the probiotic-ragi-galactomannan solution from step i) to obtain granular powdered probiotic-ragi-galactomannan; and (k) blending the galactomannans-curcuminoids powder from step (f) with powdered probiotic-ragi-galactomannan from step (j) to obtain the formulation comprising probiotic microorganisms and curcuminoids.

In one embodiment, the micelles in the micellar curcuminoids solution in step (c) are 1 to 2 microns in size.

In one embodiment, the probiotic microorganisms in step (j) are grown in the free-flowing ragi-extract-galactomannan solution till the growth reaches at least $1 \times 10^{10}$ cfu/g.

In another embodiment, the biopolymer used for the study may be fenugreek galactomannans, or others having similar physicochemical properties such as glucomannans may be used.

BRIEF DESCRIPTION OF THE FIGURES

FIG. 1 shows the serum concentration of total curcuminoids concentration after administration of standard unformulated curcuminoids (shown with closed circles) and curcuminoid-probiotic formulation (shown with closed squares) of this invention.

DETAILED DESCRIPTION OF THE INVENTION

The present invention provides herbal formulations comprising curcuminoids, probiotic microorganisms encapsulated in fenugreek (*Trigonella foenum gracum*) fiber and ragi extract matrix. Consumption of curcuminoids helps to increase antioxidant effects, reduce oxidative stress, reduce inflammatory responses and thereby to prevent diseases and maintain health. The various health beneficial effects of curcuminoids have been widely investigated and are well known. However, oral administration of curcuminoids has been shown to lead to poor bioavailability, limiting its therapeutic efficacy.

Probiotic bacteria are widely used to maintain the gut health and also have other health benefits. Probiotics administered orally have poor stability under the conditions in the gastrointestinal tract (GI tract). Though a number of probiotic formulations are available for oral delivery, no biodegradable and biocompatible natural excipients suitable for the growth and encapsulation of probiotics with antibacterial agents like curcuminoids are known. Though fenugreek galactomannans having the inherent capacity to extensively swell, form gels, thin film formation, encapsulation and emulsion stabilization effects, gum-like character, non-digestibility and amphiphilicity have been employed in the present study, similar biopolymers such as glucomannans or similar may also be useful.

Combinations for the simultaneous delivery of curcuminoids with probiotic bacteria can be of great interest, since they can offer synergistic effect to improve health functions of gut, brain etc. The health of the gut-brain axis has recently shown to be of crucial role in maintaining the healthy functioning of the mind and body. However, the simultaneous delivery of curcuminoids and probiotics pose several difficulties due to the antibacterial effect of curcuminoids. The present invention therefore provides a novel formulation for the co-delivery of curcuminoids and probiotics that ensures high bioavailability of curcuminoids and high stability for probiotics by employing natural ingredients.

The formulation comprises a unique composition of galactomannans isolated from fenugreek seeds. It is referred to herein as "galactomannan-rich fenugreek fiber".

As used herein, the term "galactomannan-rich fenugreek fiber" refers to debitterised fenugreek dietary fiber free from the phytochemicals, saponins, amino acids, alkaloids, polyphenols and flavonoids, but rich in galactomannans. Galactomannan-rich fenugreek fiber can be isolated from dried and matured fenugreek seeds by a mechanical process involving milling, sieving, gravity separation, grinding and sieving. Fenugreek fiber can be then uniformly powdered to 100 to 170 micron size, and used in the formulation of the current invention.

As used herein, the term "curcuminoids" refers to natural polyphenol compounds derived from turmeric. Curcuminoids, with bright yellow color, is the principal composition among these compounds. Curcuminoids have long been used as food, coloring agent, and traditional medicine, though absorption is often limited through oral administration.

When isolated from turmeric rhizomes, curcuminoids are a mixture of three molecules, namely curcumin, demethoxycurcuminoids (DMC) and bis-demethoxycurcuminoids (BDMC). In which curcuminoids is major about 78%, DMC is about 15% and the rest 3 to 5% is BDMC. These three are generally known as 'Curcuminoids'.

Curcuminoids powder used here is isolated from dried turmeric rhizomes by solvent extraction (using solvents such as ethanol, ethanol/water mixture, ethyl acetate, acetone, methanol, methylene dichloride etc.) followed by crystallization with ethanol, isopropanol or ethyl acetate etc.

As used herein, "unformulated curcuminoids derived from turmeric rhizomes with not less than 95% purity" refers to curcuminoids isolated from turmeric which are administered orally in their original form to the subjects, and are not encapsulated or bound by any other components. This is also referred to as "standard curcumin"

The probiotic microorganisms can be selected from the group consisting of bacteria, yeast or a combination thereof. Examples of probiotic bacteria used in the current invention are, but not limited to, *Lactobacillus acidophilus, Lactobacillus brevis, Lactobacillus rhamnosus* GG, *Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophilus, Bacillus coagulans* or a combination thereof. The probiotic yeast are selected from the group consisting of *Saccharomyces cerevisiae, Saccharomyces boulardii* etc or combination thereof.

The probiotics used in the current invention can be cultured in the ragi (finger millet, *Elusine coracana*) extract, and ragi extract is also used to encapsulate the probiotics. The ragi medium acts as a growth medium and also as encapsulating agent to protect probiotics in the GI tract. The ragi matrix used to encapsulate probiotics is also reinforced with galactomannan-rich fenugreek fiber. The encapsulated probiotic bacteria in powder form are further mixed with curcuminoids encapsulated in a matrix of galactomannan-rich fenugreek fiber. The curcuminoids used herein are extracted from the turmeric rhizome, where curcuminoids of a particular concentration is preferred in the present formulation.

The formulation disclosed in the current invention comprises 10 to 35% (w/w) of curcuminoids, 40 to 50% (w/w) of ragi probiotic powder and 40 to 50% (w/w) of galactomannan-rich fenugreek fiber. The formulation may also contain other additives or excipients as necessary.

In one embodiment, the formulation disclosed herein is administered at least once daily, at about 250 mg to 1000 mg/dose, or as sachets of 5 to 15 g/serving containing 250 to 1000 mg to provide bioavailable curcuminoids along with physiologically significant bacteria counts of greater than $10^6$ to $10^{12}$ cfu/g, which provides the desired pharmacological activity in humans. The bioavailability of curcuminoids is evaluated by the analysis of plasma concentration of curcuminoids as determined by LCMS/MS (Liquid chromatography coupled tandem mass spectrometry) measurements of the blood plasma. In one embodiment, the formulation is found to be stable when stored at room temperature.

As used herein, "effective amount" of the formulation is the amount that is required to perform the particular function in the body. Thus, any amount of probiotic that can lead to viable cell count of the microorganism in the gut after oral administration can be considered as "effective amount". As defined in paragraph 4 in Fang et al in Appln No. US20120263826 (incorporated herein by reference), cited in the current specification states that "the typical standard for any food sold with health claims from the addition of probiotics is that it contains at least $10^8$-$10^{10}$ colony forming units (CFU) of viable probiotic bacteria per serving".

Thus the novel composition can effectively deliver curcuminoids and probiotics that can offer myriad of health benefits in a single product. The formulation can also act as a prebiotics-probiotics blend in which probiotics are impregnated into, and protected by prebiotics.

The probiotic enriched curcuminoids need to be formulated to ensure the viability of the probiotics and stability of the formulation.

Hereinafter, the compositions and methods of formulation of the present invention are described herein in more detail with reference to the following methods. However, it should be understood that the following methods are provided only for illustrating the various methods that can be employed for the preparation of stable probiotics enriched bioavailable curcuminoids powder of the present invention and should not be construed as limiting the scope and spirit of the present invention.

One embodiment of the current invention is a formulation comprising probiotic microorganisms and curcuminoids in powder or granular form, wherein the formulation can be administered orally for providing health benefits. In one embodiment, the formulation is encapsulated within a matrix comprised of galactomannan-rich fenugreek fiber and ragi extract. In one embodiment, the encapsulating matrix also acts as a growth medium for the encapsulated probiotic microorganisms.

In one embodiment, the curcuminoids are strongly bound to and encapsulated in the hydrophobic pockets of the gel formed by the galactomannans chains in the galactomannan-rich fenugreek fiber and the probiotics are grown and encapsulated in the ragi extract matrix. In one embodiment, the formulation comprises a mixture of probiotic powder and curcuminoids powder, wherein the probiotic powder comprises probiotic microorganisms encapsulated in a ragi and galactomannan-rich fenugreek fiber matrix, and wherein the curcuminoids are encapsulated in a galactomannan-rich fenugreek fiber matrix.

In one embodiment, the formulation in powder form swells in the gastrointestinal tract and leaches the colloidal curcuminoids particles into the gut.

In one embodiment, it exhibits increased bioavailability, increased absorption and longer half-life of the encapsulated curcuminoids after oral administration, compared to that of the unformulated curcuminoids derived from turmeric rhizomes.

In one embodiment, the probiotic bacteria comprising the formulation are viable.

In one embodiment, the formulation disclosed in the current invention does not comprise any organic solvents.

In one embodiment, the probiotic microorganisms in the formulation disclosed in the current invention are selected from the group consisting of *Lactobacillus acidophilus, Lactobacillus acidophilus, Lactobacillus brevis, Lactobacillus rhamnosus* GG, *Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophilus, Bacillus coagulans, Saccharomyces cerevisiae*, and *Saccharomyces boulardii*.

In one embodiment, the formulation disclosed in the current invention is administered orally at a dose of 250 mg-1000 mg/dose, and wherein at least one dose of the formulation is administered daily.

In one embodiment, one dose of the formulation disclosed in the current invention, is 250-1000 mg, and comprises at least $10^6$-$10^{12}$ cfu/g of probiotic microorganisms.

In one embodiment, the concentration of curcuminoids in the formulation disclosed in the current invention is in the range of 10 to 35% w/w.

In one embodiment, the concentration of curcuminoids in the formulation disclosed in the current invention is not less than 20% w/w.

One embodiment of the current invention is a method of preparing a formulation comprising probiotic microorganisms and curcuminoids in powder or granular form, wherein the formulation can be administered orally for providing health benefits, the method comprising the steps of: (a) suspending powdered galactomannan-rich fenugreek fiber with particle size less than 100 microns in 10-15 times (w/v) water to obtain a homogenized galactomannan-rich fenugreek fiber gel phase; (b) preparing a free flowing 1 to 2% (w/v) galactomannan-rich fenugreek fiber solution; (c) adding curcuminoids powder to the galactomannan-rich fenugreek fiber solution from step (b) followed by homogenization to produce micellar curcuminoids solution comprising micelles smaller than 10 microns; (d) adding micellar curcuminoids solution from step (c) to the galactomannan-rich fenugreek ragi gel phase from step (a) followed by homogenization to obtain curcuminoids-fenugreek solution; (e) incubating the curcuminoids-fenugreek solution from step (d) for 2-4 h at 10-15° C. to obtain galactomannans-curcuminoids complexed gel; (f) converting the galactomannans-curcuminoids complexed gel from step (e) to galactomannans-curcuminoids powder; (g) making ragi extract solution from ragi seeds; (h) mixing ragi extract solution from step (g) with 2% w/w galactomannan-rich fenugreek fiber gel phase in step b) to make a free flowing ragi extract-galactomannan solution; (i) growing the probiotic microorganisms in the free-flowing ragi-extract-galactomannan solution from step (h) to obtain probiotic-ragi-galactomannan solution; (j) drying the probiotic-ragi-galactomannan solution from step i) to obtain granular powdered probiotic-ragi-galactomannan; and (k) blending the galactomannans-curcuminoids powder from step (f) with powdered probiotic-ragi-galactomannan from step (j) to obtain the formulation comprising probiotic microorganisms and curcuminoids.

In one embodiment, the micelles in the micellar curcuminoids solution in step (c) are 1-2 microns in size.

In one embodiment, the probiotic microorganisms in step (j) are grown in the free-flowing ragi-extract-galactomannan solution till the growth reaches at least $1 \times 10^{10}$ cfu/g.

It should be understood that the detailed description and specific examples, while indicating embodiments of the invention, are given by way of illustration only, because various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The terms used in this specification generally have their ordinary meanings in the art, within the context of the invention, and in the specific context where each term is used.

The use of examples anywhere in this specification including examples of any terms discussed herein is illustrative only, and in no way limits the scope and meaning of the invention or of any exemplified term. Likewise, the invention is not limited to various embodiments given in this specification.

EXAMPLES

Example 1

Debitterised fenugreek dietary fiber (galactomannan-rich fenugreek fiber) free from the phytochemicals, saponins, amino acids, alkaloids, polyphenols and flavonoids having a composition of soluble dietary fiber 80 to 90%, proteins 5 to 15%, insoluble fiber 1 to 2% and fat less than 1% was isolated from dried and matured fenugreek seeds by a mechanical process involving milling, sieving, gravity separation, grinding and sieving. High purity fenugreek fiber with low levels of proteins may also be used for the purpose. Fenugreek fiber was then uniformly powdered to 100 to 170 micron size. It was then dissolved in water by employing the methods of colloidal milling, high pressure homogenization, wet grinding and ultrasonication methods either alone or in combination to form uniform viscous solution. The fenugreek fiber solution was then mixed with 10 L of MRS (De Man, Rogosa and Sharpe agar) broth inoculated with *Lactobacillus acidophilus* to form mixture. The mixture was incubated at 35±5° C. for 48 h and checked for the bacterial count to be not less than $1 \times 10^{10}$ cfu/g.

The curcuminoids powder (>90% purity, preferably 95% purity) of required quantity was weighed and added to water (sufficient enough to make 3 to 10% w/v) containing 1 to 2% (w/v) of fenugreek fiber and passed through a colloidal mill. It was further subjected to homogenization or ultrasonication or in combination to get a uniform solution of around 1 μm micellar size. d-α-Tocopheryl polyethylene glycol 1000 succinate (TPGS) (1 to 2% by the weight of curcuminoids) or sugar esters were also added to adjust the particle size and uniformity of curcuminoids solution. Curcuminoids powder used here was isolated from dried turmeric rhizomes by solvent extraction (using solvents such as ethanol, ethanol/water mixture, ethyl acetate, acetone, methanol, methylene dichloride etc.) followed by crystallization with ethanol, isopropanol or ethyl acetate etc.

Curcuminoids solution was then slowly mixed with fenugreek fiber solution containing probiotic bacteria to get a uniform solution. The solution was dried under vacuum using the methods of freeze drying, spray drying, vacuum belt drying or any other drying under the lowest temperature possible. The powder thus obtained was subjected to mild grinding, and sieving to get probiotics enriched bioavailable curcuminoids powder. The probiotic enriched curcuminoids powder was evaluated for the probiotic content, which shows the viable microorganism count sufficient to provide the desired pharmacological effect. The results were as shown below
*Lactobacillus* growth before freeze drying—$1.3 \times 10^8$ cfu/g
*Lactobacillus* growth after freeze drying—$7.4 \times 10^7$ cfu/g
*Lactobacillus* growth before spray drying—$1.3 \times 10^8$ cfu/g
*Lactobacillus* growth after spray drying—$5.6 \times 10^6$ cfu/g Example 2

Fenugreek fiber and curcuminoids solutions were prepared separately as mentioned in Example 1. The solutions were mixed together and dried under vacuum by freeze drying, spray drying, vacuum belt drying, vacuum oven or any other drying under the lowest temperature possible. The powder obtained is dissolved in water and inoculated with probiotic bacteria strains like *Lactobacillus acidophilus* and incubated at 35±5° C. for 48 h and checked for the bacterial count to be not less than $1 \times 10^{10}$ cfu/g. The final solution was then dried by freeze drying, spray drying, vacuum belt drying or any other drying under the lowest temperature possible to get probiotic enriched bioavailable curcuminoids powder. The viable probiotic microbial content in powder was evaluated, the results are shown below:
*Lactobacillus* growth before freeze drying—$1.1 \times 10^8$ cfu/g
*Lactobacillus* growth after freeze drying—$6.9 \times 10^7$ cfu/g
*Lactobacillus* growth before spray drying—$1.1 \times 10^8$ cfu/g
*Lactobacillus* growth after spray drying—$5.1 \times 10^6$ cfu/g Example 3

The solutions of fenugreek fiber and curcuminoids powder were prepared separately as mentioned in Example 1. In addition, 5 to 10% (w/w) of either ragi powder (RP) or ragi-water extract (RWP) powder was also added to fenugreek fiber solution during its preparation. The bacterial culture was added to fenugreek fiber solution with RP or RWP and incubated at 35±5° C. for 48 h and checked for the bacterial count to be not less than $1 \times 10^{10}$ cfu/g. The solution was then mixed with curcuminoids solution and was dried as mentioned in Method 1 to get probiotic-enriched bioavailable curcuminoids. The viable probiotic content in powder was evaluated, the results are shown below
*Lactobacillus* growth before freeze drying—$3.6 \times 10^9$ cfu/g
*Lactobacillus* growth after freeze drying—$2.8 \times 10^8$ cfu/g
*Lactobacillus* growth before spray drying—$3.6 \times 10^9$ cfu/g
*Lactobacillus* growth after spray drying—$7.2 \times 10^7$ cfu/g Example 4

The solutions of fenugreek fiber and curcuminoids solution were separately prepared as mentioned in Example 1. The probiotic bacteria were separately grown in a solution of either ragi powder (RP) or ragi-water extract RWP, preferably RWP and mixed with both fenugreek fiber and curcuminoids solution. The homogeneous solution thus obtained was dried as mentioned in Example 1 to get probiotic-enriched bioavailable curcuminoids.

The viable probiotic microbial content in powder was evaluated, the results are shown below:
*Lactobacillus* growth before Freeze drying—$1.5 \times 10^{11}$ cfu/g
*Lactobacillus* growth after Freeze drying—$6.2 \times 10^9$ cfu/g
*Lactobacillus* growth before spray drying—$1.5 \times 10^{11}$ cfu/g
*Lactobacillus* growth after spray drying—$3.8 \times 10^8$ cfu/g Example 5

In this method, probiotic-enriched bioavailable curcuminoids powder (prepared by methods mentioned in Example 1 or Example 2) and probiotic-enriched ragi extract powder were separately prepared. Probiotic-enriched ragi extract powder was prepared by incubating probiotics in the water extract of ragi at 37° C. for 24 h and then converting to powder form by any of the methods mentioned in above examples. Both the powders are blended together to produce probiotic-enriched bioavailable curcuminoids. The viable probiotic content in individual powders and mixture were evaluated, the results are shown below:
Probiotic content in individual powder mixture: *Lactobacillus* growth in ragi powder—$2.7 \times 10^{10}$ cfu/g
*Lactobacillus* growth in curcuminoids/fenugreek fiber—$2.1 \times 10^7$ cfu/g
Probiotic content in blended powder mixture:
*Lactobacillus* growth in the blend prepared above—$2.32 \times 10^8$ cfu/g
After
   One week—$2.3 \times 10^8$ cfu/g
   Two weeks—$2.1 \times 10^8$ cfu/g
   Three weeks—$2.0 \times 10^8$ cfu/g
   Four weeks—$2.31 \times 10^8$ cfu/g Example 6

The solutions of fenugreek fiber, curcuminoids and ragi solution were separately prepared (as mentioned in Example 1). The solutions were mixed together and dried under vacuum by freeze drying, spray drying, vacuum belt drying, and vacuum oven or any other drying under the lowest temperature possible. The probiotic bacteria were separately prepared and the bacterial count was found to be $1 \times 10^{10}$ cfu/g. The mixture of curcuminoids and fenugreek fiber was homogenized with ragi powder in which the probiotic bacteria was inoculated and incubated at 35±5° C. for 48 h. The bacterial count was found to be not less than $1 \times 10^{10}$ cfu/g. Then the final solution dried under freeze drying, spray drying, vacuum belt drying or any other drying under the lowest temperature possible to get probiotic enriched bioavailable curcuminoid powder. The viable probiotic content in powder was evaluated, the results are shown below.
*Lactobacillus* growth before freeze drying—$3.2 \times 10^8$ cfu/g
*Lactobacillus* growth after freeze drying—$3.1 \times 10^8$ cfu/g Example 7

Fenugreek galactomannans (85 g) was fine powdered to less than 100 micron size and suspended in 20 times excess of water, and homogenized till a uniform (homogeneous) gel without any swelled particles were obtained.

In another vessel, we made 1 to 2% galactomannans free flowing solution and added curcuminoid powder with not less than 92% purity (22 g in 350 ml water) slowly with homogenization using colloidal mills or rotor-strator homogenizers. Curcuminoids powder of smallest particle size from 5 to 200 micron size may be used. The solution was then subjected to extensive homogenization to produce small micelles (less than 10 micron size, preferably around 1 to 2 microns.

Curcuminoid solution was then slowly mixed to the fenugreek galactomannans gel phase and again homogenized for uniform distribution of curcuminoids solution in the gel phase without any clumping or swelled gel separation. The mixture was then kept for 2 to 4 h at 10 to 15° C. for the formation of gels and it is further subjected to freeze drying to produce powder. Alternatively, the gel can also be diluted to a free flowing solution without any settlement and can be spray dried. The gel can also be evaporated under controlled temperature (70° C.) under vacuum to powder form (114-116 g).

Ragi seeds (200 g) were ground with water to a paste consistency and was then extracted with water (600 mL each for each wash) (2 to 3 times) at 50 to 70° C. The water extract was filtered from the residue and concentrated under vacuum to a brix (total dissolved solids) level of 20 to 25% w/v. It was then spray dried to get the ragi extract powder. 26.6 g of ragi extract powder is prepared to solution by using water and mixed with 2% w/w of fenugreek galactomannans. It was again homogenized to get a free flowing solution of ragi extract powder.

Probiotics bacteria were inoculated (10 mL LAB/100 mL extract) and incubated for 24 to 48 h at 35 to 37° C. Once the growth reached to not less than $1 \times 10^{10}$ cfu/g, it was also converted to a powder by using any of the methods explained above.

As a next step, Curcuminoids-galactomannan powder and ragi-galactomannan-probiotics powder were blended together to produce probiotics fortified curcuminoids powder exhibiting bioavailability of curcuminoids and viability of probiotics.

Example 8

Seven human volunteers between the age group of 20 to 30 years were selected. All the volunteers were healthy and not involved in any medication or health supplementation. The volunteers were not allowed to take turmeric-containing food since two days prior to the test. The zero time blood samples was withdrawn, followed by randomized treatment with either the formulation disclosed herein, comprising probiotics (not less than $1 \times 10^8$ cfu/g) and curcuminoids in a galactomannan rich fenugreek fiber and ragi matrix (500 mg; consists of 20% curcuminoids) or standard curcuminoids (500 mg consist of 95% curcuminoids) capsules along with 200 mL of plain drinking water. Four millilitres of blood sample were withdrawn at 0.5, 1, 3, 5 and 8 h post-dose time points employing an indwelling venous cannula; serum was separated by centrifugation at 12000 rpm for 10 min at 4° C. 1 mL of the serum was then used to analyse curcuminoids content by LC MS/MS. Serum was deep-frozen at −80° C. till analysis.

Curcuminoids in serum were extracted and subjected to UPLC-ESI-MS/MS analyses, as reported by Krishnakumar et al. (2015). Briefly, 1 mL of serum was treated extracted with 4×5 mL of 5% (v/v) methanol containing ethyl acetate and evaporated to dryness at 45° C. under nitrogen atmosphere. The residue was then made up to 1 mL with methanol, filtered through a 0.45 µm syringe filter and 5 µL was injected. Separation was achieved with Agilent Eclipse plus C-18 RRHD column (3×50 mm; 1.8 µm) kept at 40° C. The mobile phase consisted of (A) 5 mM ammonium acetate (pH 4.5 adjusted with acetic acid) and (B) acetonitrile containing 0.1% acetic acid, set at a linear gradient of 40 to 60% B within 7 min at 0.3 mL/min flow rate.

Analysis of curcuminoids content in serum for 7 volunteers is depicted in FIG. 1, considerable enhancement in bioavailability, almost 31 times of enhancement in area under serum concentration verses time plot on an average, of curcuminoids was observed after the consumption of the newly developed formulation disclosed in the current invention.

What is claimed is:

1. A product formulation comprising a mixture of probiotic powder and curcuminoids powder,
    wherein the probiotic powder comprises probiotic microorganisms encapsulated in a ragi and galactomannan-rich fenugreek fiber matrix,
    wherein the curcuminoids are encapsulated in a galactomannan-rich fenugreek fiber matrix, and
    wherein the product is formulated for oral administration.
2. The product formulation of claim 1, wherein the ragi matrix is a growth medium for the encapsulated probiotics.
3. The product formulation of 1, wherein the formulation exhibits increased bioavailability, increased absorption and longer half-life of the encapsulated curcuminoids after oral administration, compared to that of unformulated curcuminoids derived from turmeric rhizomes.
4. The product formulation of claim 1, wherein the probiotic microorganisms in the formulation are viable.
5. The product formulation of claim 1, wherein the probiotic microorganisms are selected from the group consisting of *Lactobacillus acidophilus*, *Lactobacillus acidophilus*, *Lactobacillus brevis*, *Lactobacillus rhamnosus* GG, *Lactobacillus bulgaricus*, *Lactobacillus plantarum*, *Lactobacillus reuteri*, *Lactobacillus casei*, *Lactobacillus paracasei*, *Bifidobacterium infantis*, *Bifidobacterium lactis*, *Bifidobacterium bifidum*, *Streptococcus thermophilus*, *Bacillus coagulans*, *Saccharomyces cerevisiae*, and *Saccharomyces boulardii*.
6. The product formulation of claim 1, wherein a single dose comprises 250 mg-1000 mg of the formulation.
7. The product formulation of claim 6, wherein the single dose of the formulation comprises at least $10^6$ to $10^{12}$ cfu/g of probiotic microorganisms.
8. The product formulation of claim 1, wherein the formulation comprises 10 to 35% w/w curcuminoids.
9. A method of preparing the product formulation as set forth in claim 1, the method comprising the steps of:
    a) suspending powdered galactomannan-rich fenugreek fiber with particle size less than 100 microns in 10-15 times (w/v) water to obtain a homogenized galactomannan-rich fenugreek fiber gel phase;
    b) preparing a free flowing 12% (w/v) galactomannan-rich fenugreek fiber solution;
    c) adding curcuminoids powder to the galactomannan-rich fenugreek fiber solution from step (b) followed by homogenization to produce micellar curcuminoids solution comprising micelles smaller than 10 microns;
    d) adding micellar curcuminoids solution from step (c) to the galactomannan-rich fenugreek fiber gel phase from step (a) followed by homogenization to obtain curcuminoids-fenugreek solution;

e) incubating the curcuminoids-fenugreek solution from step (d) for 2-4 h at 10-15° C. to obtain galactomannans-curcuminoids complexed gel;
f) converting the galactomannans-curcuminoids complexed gel from step (e) to galactomannans-curcuminoids powder;
g) making ragi extract solution from ragi seeds;
h) mixing the ragi extract solution from step (g) with 2% w/w galactomannan-rich fenugreek fiber gel phase in step b) to make a free flowing ragi-extract-galactomannan solution;
i) growing probiotic microorganisms in the free-flowing ragi-extract-galactomannan solution from step (h) to obtain probiotic-ragi-galactomannan solution;
j) drying the probiotic-ragi-galactomannan solution from step (i) to obtain granular powdered probiotic-ragi-galactomannan; and
k) blending the galactomannans-curcuminoids powder from step (f) with powdered probiotic-ragi-galactomannan from step (j) to obtain the formulation comprising probiotic microorganisms and curcuminoids.

10. The method of claim 9, wherein the micelles in the micellar curcuminoids solution in step (c) are 1-2 microns in size.

11. The method of claim 9, wherein the probiotic microorganisms in step (j) are grown in the ragi-extract-galactomannan solution till the growth reaches at least $1\times10^{10}$ cfu/g.

* * * * *